United States Patent [19]

Johnson

[11] 4,209,318
[45] Jun. 24, 1980

[54] HERBICIDAL ESTERS OF 4-TRIFLUOROMETHYL-3-CARBOXAMIDO-4-NITRO DIPHENYL ETHERS

[75] Inventor: Wayne O. Johnson, Warminster, Pa.

[73] Assignee: Rohm and Haas Company, Philadelphia, Pa.

[21] Appl. No.: 927,062

[22] Filed: Jul. 20, 1978

Related U.S. Application Data

[62] Division of Ser. No. 747,466, Dec. 3, 1976, abandoned.

[51] Int. Cl.² .................. A01N 9/20; C07C 103/75; C07C 121/60; A01N 9/24
[52] U.S. Cl. ........................... 71/88; 71/105; 71/111; 71/118; 260/348.45; 260/465 D; 260/559 R; 560/21
[58] Field of Search ........... 260/558 P, 559 R, 348.45, 260/465 D; 71/88, 118, 105

[56] References Cited

U.S. PATENT DOCUMENTS

| | | | |
|---|---|---|---|
| 3,798,276 | 3/1974 | Bayer | 260/612 R |
| 3,928,416 | 12/1975 | Bayer | 260/471 R |
| 4,002,662 | 1/1977 | Theissen | 260/465 D |
| 4,021,224 | 5/1977 | Pallos | 71/88 |

*Primary Examiner*—Glennon H. Hollrah
*Assistant Examiner*—Lisa Jones
*Attorney, Agent, or Firm*—Terence P. Strobaugh

[57] ABSTRACT

Compounds of the formula

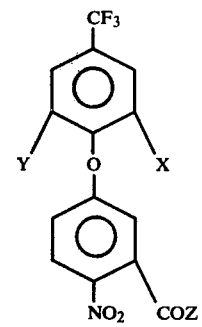

wherein
X is a hydrogen atom, a halogen atom, a trihalomethyl group, an alkyl group, or a cyano group,
Y is a hydrogen atom, a halogen atom, or a trihalomethyl group, and
Z is a group of the formula —OZ' or —NRZ', wherein Z' is an alkenyl group, an alkynyl group, an aralkenyl group, a cycloalkenyl group, or an epoxyalkyl group and R is a hydrogen atom or an alkyl group, and compositions containing these compounds exhibit herbicidal activity.

13 Claims, No Drawings

HERBICIDAL ESTERS OF 4-TRIFLUOROMETHYL-3-CARBOXAMIDO-4-NITRO DIPHENYL ETHERS

This is a division of application Ser. No. 747,466 filed Dec. 3, 1976 now abandoned.

This invention relates to novel compounds which show activity as herbicides, to novel herbicidal compositions which contain these compounds, and to new methods of controlling weeds with these herbicidal compositions.

Certain diphenyl ethers have been shown to be effective weed control agents. However, the herbicidal effectiveness of a given diphenyl ether cannot be predicted from an examination of the substituent groups attached to the phenyl rings in the ether, and often quite closely related compounds will have quite different weed control abilities. Various diphenyl ethers may have overlapping or complementary areas of activity or selectivity, and can thus be useful in combination to control a variety of weeds upon application of a single composition. Furthermore, the diphenyl ethers heretofore disclosed as herbicides are not completely effective. An ideal herbicide should give selective weed control, over the full growing season, with a single administration at low rates of application. It should be able to control all common weeds by killing them as the seed, the germinating seed, the seedling, and the growing plant. At the same time, the herbicide should not be phytotoxic to the crops to which it is applied and should decompose or otherwise be dissipated so as not to poison the soil permanently. The known diphenyl ether herbicides fall short of these ideals, and it would thus be desirable to have new herbicides which show even more selective control of undesirable plants among desirable crop plants or which complement known herbicides in activity.

In accordance with the present invention, there is provided a new class of novel diphenyl ethers having the formula

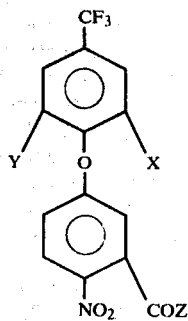

wherein

X is a hydrogen atom, a halogen atom, preferably a fluorine atom or a chlorine atom, a trihalomethyl group, preferably a trifluoromethyl group, a ($C_1$–$C_4$)alkyl group, preferably a methyl group, or a cyano group, Y is a hydrogen atom, a halogen atom, preferably a fluorine atom or a chlorine atom, or a trihalomethyl group, preferably a trifluoromethyl group, and Z is a group of the formula —OZ' or —NRZ', wherein Z' is an alkenyl group, preferably having 2 to 6 carbon atoms, a haloalkenyl group, preferably having 3 to 6 carbon atoms, a haloalkynyl group, preferably having 3 to 6 carbon atoms, an aralkenyl group, preferably having 8 to 12 carbon atoms, most preferably a phenyl or halo-, methyl-, or nitro-substituted phenyl($C_2$–$C_4$)alkenyl group, a cycloalkenyl group, preferably monocyclic and having 4 to 7 carbon atoms, or an epoxyalkyl group, preferably having 3 to 6 carbon atoms, and R is a hydrogen atom or an alkyl group, preferably having 1 to 4 carbon atoms.

The Z' and R substituents can have either a straight- or branched-chain configuration. When Z' is a halo-substituted unsaturated hydrocarbyl group, there are preferably 1 or 2 substituents.

These novel compounds have been found to show unexpected activity as weed control agents. In a preferred embodiment of the invention, X is a halogen atom, most preferably a chlorine atom, Y is a hydrogen atom or a halogen atom, preferably a chlorine atom and Z is a group of the formula —OZ'. In another preferred embodiment, Z is an alkenyloxy group, most preferably an allyloxy group.

Examples of the compounds of the invention embraced by Formula I include:

Allyl 2-nitro-5-(2-chloro-α,α,α-trifluoro-p-tolyloxy)benzoate

Propynyl 2-nitro-5-(2-cyano-α,α,α-trifluoro-p-tolyloxy)benzoate

Glycidyl 2-nitro-5-(2-cyano-6,α,α,α-tetrafluoro-p-tolyloxy)benzoate

Δ$^2$-Cyclohexenyl 2-nitro-5-(α,α,α,α',α',α'-hexafluoro-2,4-xylyloxy)benzoate

Vinyl 2-nitro-5-(2,6-dichloro-α,α,α-trifluoro-p-tolyloxy)benzoate

Δ$^3$-Butenyl 2-nitro-5-(2-chloro-α,α,α-trifluoro-p-tolyloxy)benzoate

β-Methylallyl 2-nitro-5-(2-chloro-α,α,α-trifluoro-p-tolyloxy)benzoate

α,α-Dimethylallyl 2-nitro-5-(6-chloro-2-methyl-α,α,α-trifluoro-p-tolyloxy)benzoate Δ$^3$-Cyclopentenyl 2-nitro-5-(2-bromo-α,α,α-trifluoro-p-tolyloxy)benzoate Δ$^2$-Butenyl 2-nitro-5-(α,α,α-trifluoro-p-tolyloxy)benzoate Allyl 2-nitro-5-(2-cyano-α,α,α-trifluoro-p-tolyloxy)benzoate β-Stynyl 2-nitro-5-(2-cyano-6-chloro-α,α,α-trifluoro-p-tolyloxy)benzoate α-Methyl-Δ$^2$-cyclobutenyl 2-nitro-5-(2-chloro-α,α,α-trifluoro-p-tolyloxy)benzoate γ,γ-Dimethylallyl 2-nitro-5-(2,6-dichloro-α,α,α-trifluoro-p-tolyloxy)benzoate 2-Chloroallyl 2-nitro-5-(2-chloro-α,α,α-trifluoro-p-tolyloxy)benzoate 3-Chloropropynyl 2-nitro-5-(2,6-dichloro-α,α,α-trifluoro-p-tolyloxy)benzoate 2,3-Dichloroallyl 2-nitro-5-(2-chloro-α,α,α-trifluoro-p-tolyloxy)benzoate 2,3,3-Trichloroallyl 2-nitro-5-(2-cyano-α,α,α-trifluoro-p-tolyloxy)benzoate N-Allyl-2-nitro-5-(2-chloro-α,α,α-trifluoro-p-tolyloxy)benzamide N-Propynyl-2-nitro-5-(2-cyano-α,α,α-trifluoro-p-tolyloxy)benzamide N-Glycidyl-N-methyl-2-nitro-5-(2-cyano-6,α,α,α-tetrafluoro-p-tolyloxy)benzamide N-Δ²-Cyclohexenyl-2-nitro-5-($\alpha,\alpha,\alpha,\alpha',\alpha',\alpha'$-hexafluoro-2,4-xylyloxy)benzamide N-Vinyl-2-nitro-5-(2,6-dichloro-$\alpha,\alpha,\alpha$-trifluoro-p-tolyloxy)benzamide N-Δ³-Butenyl-N-ethyl-2-nitro-5-(2-chloro-$\alpha,\alpha,\alpha$-trifluoro-p-tolyloxy)benzamide N-β-Methylallyl-2-nitro-5-(2-bromo-$\alpha,\alpha,\alpha$-trifluoro-p-tolyloxy)benzamide N-$\alpha,\alpha$-dimethylallyl-2-nitro-5-(6-chloro-2-methyl-$\alpha,\alpha,\alpha$-trifluoro-p-tolyloxy)benzamide N-Δ³-Cyclopentenyl-N-butyl-2-nitro-5-(2-bromo-$\alpha,\alpha,\alpha$-trifluoro-p-tolyloxy)benzamide N-Δ²-Butenyl-2-nitro-5-($\alpha,\alpha,\alpha$-trifluoro-p-tolyloxy)-benzamide N-Allyl-N-methyl 2-nitro-5-(2-cyano-$\alpha,\alpha,\alpha$-trifluoro-p-tolyloxy)benzamide N-β-Stynyl-2-nitro-5-(2-cyano-6-chloro-$\alpha,\alpha,\alpha$-trifluoro-p-tolyloxy)benzamide N-α-Methyl-Δ²-cyclobutenyl-2-nitro-5-(2-chloro-$\alpha,\alpha,\alpha$-trifluoro-p-tolyloxy)benzamide N-γ,γ-Dimethylallyl-2-nitro-5-(2,6-dichloro-$\alpha,\alpha,\alpha$-trifluoro-p-tolyloxy)benzamide N-2-Chloroallyl-2-nitro-5-(2-chloro-$\alpha,\alpha,\alpha$-trifluoro-p-tolyloxy)benzamide N-3-Chloropropynyl-N-ethyl-2-nitro-5-(2,6-dichloro-$\alpha,\alpha,\alpha$-trifluoro-p-tolyloxy)benzamide N-2,3-Dichloroallyl-2-nitro-5-(2-chloro-$\alpha,\alpha,\alpha$-trifluoro-p-tolyloxy)benzamide N-2,3,3-Trichloroallyl-2-nitro-5-(2-cyano-$\alpha,\alpha,\alpha$-trifluoro-p-tolyloxy)benzamide and the like.

The novel diphenyl ethers of the invention are useful both as preemergence and as postemergence herbicides. Preemergence herbicides are ordinarily used to treat the soil in which the desired crop is to be planted by application either before seeding, during seeding, or, as in most applications, after seeding and before the crop emerges. Post-emergence herbicides are those which are applied after the plants have emerged and during their growth period. Compounds of the invention are particularly active against broadleaf weeds.

Among the crops on which the diphenyl ethers of the invention can be advantageously employed are, for example, soybeans, corn, wheat, barley, rice and other cereal crops and the like.

When used in transplanted rice crops, the ethers can be applied either preemergence or postemergence to the weeds—that is, they can be applied to the growth medium of the transplanted plants either before the weed plants have emerged or while they are in their early stages of growth. The ethers can be applied to the growth medium either before or after the rice has been transplanted to that medium.

The diphenyl ethers of the invention can be applied in any amount which will give the desired degree of weed control. A preferred rate of application of the herbicides of the invention is from about 0.1 to about 12, and most preferably about 0.25 to 4, pounds of the diphenyl ether per acre.

Under some conditions, the diphenyl ethers of the invention may be advantageously incorporated into the soil or other growth medium prior to planting a crop. This incorporation can be carried out by any convenient means, including by simple mixing with the soil, by applying the diphenyl ether to the surface of the soil and then disking or dragging into the soil to the desired depth, or by employing a liquid carried to accomplish the necessary penetration and impregnation.

A diphenyl ether of the invention can be applied to the growth medium or to plants to be treated either by itself or, as is generally done, as a component in a herbicidal composition or formulation which also comprises an agronomically acceptable carrier. By agronomically-acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The diphenyl ether compounds of this invention can be dissolved in any appropriate solvent. Examples of solvents which are useful in the practice of this invention include alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as a granular fuller's earth, vermiculite, ground corn cobs, seed hulls, including bran or other grainhulls, or similar material. A solution of one or more of the diphenyl ethers in a volatile organic solvent is then removed by evaporation. The granular material can have any suitable size, with a preferable size range of 16 to 60 mesh. The diphenyl ether will usually comprise about 2 to 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular fomulations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the methods of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

Carboxylic Acids and Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts Carbamic Acid Derivatives ethyl N,N-di-(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-clorophenyl)carbamate
methyl N-(3,4-dichlorophenyl)carbamate Phenols dinitro-O-(sec-butyl)phenol and its salts
pentachlorophenol and its salts Substituted Ureas 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
dichloral urea Substituted Triazines 2-chloro-4,6-bis(ethylamino)-s-triazine
2-chloro-4-ethylamino-6-isopropylamino)-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2methoxy-4-ethylamino-6-isopropylamino-s-triazine
2-methylmercapto-4-(2-methoxyethylamino)-6-isopropoamino-s-triazine Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4-dinitro-4-trifluoromethyldiphenyl ether
2,4-dichloro-3'-methoxy-4'-nitrodiphenyl ether 2-chloro-4-trifluoromethyl-3'-ethoxy-4'-nitrodiphenyl ether
2-chloro-4-trifluoromethyl-4'-nitrodiphenyl ether
2-chloro-4-trifluoromethyl-3'-carbethoxy-4'-nitrodiphenyl ether
2,4-dichloro-3'-carbomethoxy-4'-nitrodiphenyl ether

Anilides

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-α,α-dimethylvaleramide
N-isopropyl-N-phenylchloroacetamide
N-n-butoxymethyl-N-(2,6-diethylphenyl)chloroacetamide
N-n-methoxymethyl-N-(2,6-diethylphenyl)chloroacetamide

Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

Nitriles 2,6-dichlorobenzonitrile
diphenylacetonitrile
3,5-dibromo-4-hydroxybenzonitrile
3,5-diiodo-4-hydroxybenzonitrile

Other Organic Herbicides 2-chloro-N,N-diallylacetamide
N-(1,1-dimethyl-2-propynyl)-3,5-dichlorobenzamide
maleic hydrazide
3-amino-1,2,4-triazole
monosodium methanearsonate
disodium methanearsonate
N,N-dimethyl-α,α-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
O-(2,4-dichlorophenyl)-O-methyl-isopropylphosphoramidothioate
4-amino-3,5,6-trichloropicolinic acid
2,3-dichloro-1,4-naphthoquinone
di(methoxythiocarbonyl)disulfide
3-isopropyl-1H-2,1,3-benzothiazidzin-(4)3H-one-2,2-dioxide
6,7-dihydrodipyrido[1,2-a:2',1'-c]pyrazidinium salts
1,1'-dimethyl-4,4'bipyridinium salts
3,4,5,6-tetrahydro-3,5-dimethyl-2-thio-2H-1,3,5-thiadiazine.

When mixtures of herbicides are employed, the relative proportions which are used will depend upon the crop to be treated and the degree of selectivity in weed control which is desired.

The ethers of the invention can be prepared by esterification or amidification of a diphenyl ether of the formula

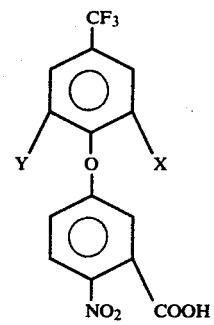

wherein X and Y are as defined above, or of the corresponding acid chloride, with an alcohol of the formula $$Z'—OH \qquad (IIIa)$$

or with an amine of the formula $$Z'—NHR \qquad (IIIb)$$

wherein Z' and R are as defined above.

The esterification is generally carried out at a temperature of about 0° to about 120° C., and preferably at room temperature, optionally in the presence of an inert organic solvent, such as a hydrocarbon or chlorinated hydrocarbon. In the esterification reaction, one equivalent of the alcohol is generally employed, although excess alcohol can be used as a solvent in the reaction. When the acid chloride is used as the reagent, an acid scavenger is generally used. In the esterification reaction, typical acid scavengers include inorganic bases, such as potassium hydroxide, and amines, such as 2,6-lutidine, while in the amidification reaction, an excess of one equivalent of the amine starting reagent can function as the acid scavenger. Other conventional esterification and amidification techniques, such as transesterification, transamination, the Schotten-Baumann reaction, and the like, can also be used.

A modification of the above preparative method for preparing the esters of the invention involves the reaction of a metal salt, such as the sodium salt, of an acid of Formula II with a halide of the formula Z'—Hal, where Hal is a halogen, preferably chlorine or bromine, atom. This reaction is generally carried out at a temperature of about 0° to about 120° C., preferably room temperature, and in an inert organic solvent, such as benzene.

Another route to the compounds of the invention involves the nitration of a diphenyl ether of the formula:

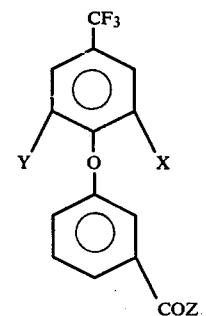

wherein X, Y, and Z are as defined above, using typical nitrating agents such as potassium nitrate in sulfuric acid, acetyl nitrate, mixed sulfuric acid/nitric acid, nitrosonium tetrafluoroborate, and the like. The nitration reaction is generally carried out at about −20° to about 100° C., preferably about 0° to about 5° C., optionally in the presence of an inert organic solvent, such as methylene chloride or other chlorinated hydrocarbon.

Ethers of the invention can also be prepared by condensing a phenol of the formula

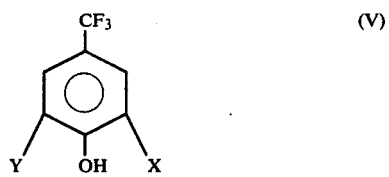 (V)

wherein X and Y are as defined above with a substituted halobenzene of the formula

 (VI)

wherein $X^1$ is a halogen atom, preferably a fluorine atom, and Z is as defined above. This reaction is generally carried out at a temperature of about 0° to about 250° C., preferably about 75° to about 200° C., optionally in the presence of an appropriate solvent, such as sulfolane, dimethylsulfoxide, dimethylformamide, hexamethylphosphoroustriamide, or other inert polar organic solvent.

The diphenyl ether precursors can be prepared by reacting a suitably substituted phenol, or the potassium or sodium salt of the phenol, with a suitably substituted halobenzene, such as a chloro- or fluorobenzene in the presence of an alkaline agent. Such precursors and their preparation are described in U.S. Pat. No. 3,928,416, of Bayer et al., granted Dec. 23, 1975, which is incorporated herein by reference.

The following examples will further illustrate this invention but are not intended to limit it in any way. In Table I, typical diphenyl ethers of the invention are listed with their elemental analyses. Specific, illustrative preparations of the compounds of Examples 1, 7, and 12 are set forth after Table I. All temperatures are in degrees centigrade and parts and percentages are by weight unless otherwise indicated.

TABLE I
DIPHENYL ETHERS - PHYSICAL DATA

| Example No. | R' | m.p.* | % C | % H | % N | % F |
|---|---|---|---|---|---|---|
| 1 | —OCH$_2$CH=CH$_2$ | found | 51.15 | 2.73 | 3.83 | 14.10 |
|   |   | calc. | 50.82 | 2.76 | 3.48 | 14.18 |
| 2 | —OCH$_2$CH=CHCH$_3$ | found | 53.0 | 3.5 | 3.5 | 12.9 |
|   |   | calc. | (51.9) | (3.2) | (3.4) | (13.7) |
| 3 | —OCH$_2$C(CH$_3$)=CH$_2$ | found | 53.1 | 3.5 | 3.6 | 12.2 |
|   |   | calc. | (51.9) | (3.2) | (3.4) | (13.7) |
| 4 | —OCH(CH$_3$)—CH=CH$_2$ | found | 52.6 | 3.2 | 3.6 | 13.1 |
|   |   | calc. | (51.9) | (3.2) | (3.4) | (13.7) |
| 5 | —OCH$_2$CH$_2$CH=CH$_2$ | found | 52.7 | 3.3 | 3.7 | 13.1 |
|   |   | calc. | (51.9) | (3.2) | (3.4) | (13.7) |
| 6 | —OCH$_2$CH=C(CH$_3$)$_2$ | found | 54.4 | 4.0 | 3.4 | 12.5 |
|   |   | calc. | (53.2) | (3.5) | (3.3) | (13.3) |
| 7 | —OC(CH$_3$)$_2$—CH=CH$_2$ | found | 55.6 | 4.3 | 3.4 | 12.6 |
|   |   | calc. | (53.2) | (3.5) | (3.3) | (13.3) |
| 8 | —OCH$_2$C≡CH | found | 51.5 | 2.3 | 3.6 | 13.8 |
|   |   | calc. | (51.1) | (2.3) | (3.5) | (14.3) |
| 9 | —OCH(CH$_3$)—C≡CH | found | 53.2 | 2.9 | 3.5 | 13.1 |
|   |   | calc. | (52.3) | (2.7) | (3.4) | (13.8) |
| 10 | —OCH$_2$C(Cl)=CH$_2$ | found | 46.8 | 2.8 | 3.2 | 11.0 |
|   |   | calc. | (46.9) | (2.3) | (3.2) | (13.1) |
| 11 | —OCH$_2$CH—CH$_2$ (epoxide) | found | 49.8 | 3.0 | 3.4 | 13.1 |
|   |   | calc. | (49.0) | (2.7) | (3.4) | (13.7) |
| 12 | —NHCH$_2$CH=CH$_2$ | found | 50.34 | 3.0 | 7.21 | 14.10 |
|   |   | calc. | (51.0) | (3.0) | (7.0) | (14.2) |

*The compounds of Examples 1 to 11 are oils

EXAMPLE 1

Preparation of Allyl
2-nitro-5-(2-chloro-α,α,α-trifluoro-p-tolyloxy)benzoate

Oxalyl chloride (51 g. 0.4 mole) is added dropwise to a solution of 2-nitro-5-(2-chloro-α,α,α-trifluoro-p-tolyloxy)benzoic acid (109 g. 0.3 mole) in benzene (200 ml.) and the solution heated under reflux for 18 hours. Solvent and excess reagent are stripped off and fresh benzene (250 ml.) and allyl alcohol (18 g. 0.31 mole) are added, followed by 2,6-lutidine (35 g. 0.32 mole) in benzene (50 ml.), added dropwise at room temperature. The mixture is diluted with ether, washed with water, dried, and filtered through a little silica gel. The solvents are removed, and, after standing, the residue solidifies and is slurried in hexane to give 114 g. of allyl-2-nitro-5-(2-chloro-α,α,α-trifluoro-p-tolyloxy)benzoate as a waxy solid.

EXAMPLE 7

Preparation of α,α-Dimethylallyl
2-nitro-5-(2-chloro-α,α,α-trifluoro-p-tolyloxy)benzoate.

To a solution of 8.7 g (0.10 mol) of 2-methyl-3-buten-2-ol in 100 ml of tetrahydrofuran at 25° is added portionwise 4.2 g of a 57% oil dispersion of sodium hydride (0.10 mol). The solution is stirred magnetically until gas evolution ceases. A solution of 38.0 g (0.10 mol) of 2-nitro-5-(2-chloro-α,α,α-trifluoro-p-tolyloxy)benzoyl chloride in 50 ml of benzene is added dropwise with stirring. After 3 hours the solution is evaporated to dryness under vacuum, diluted with 200 ml of ether, extracted with 100 ml of dilute aqueous sodium bicarbonate solution, extracted with 100 ml of water and dried.

The solution is vacuum filtered through a short column of silica gel, and then evaporated under vacuum to give 22.55 g of α,α-dimethylallyl 2-nitro-5-(2chloro-α,α,α-trifluoro-p-tolyloxy)benzoate as a light yellow oil.

EXAMPLE 12

Preparation of
N-Allyl-2-nitro-5-(2-chloro-α,α,α-trifluoro-p-tolyloxy)-benzamide A solution of 2-nitro-5-(2-chloro-α,α,α-trifluoro-p-tolyloxy)benzoyl chloride (0.0875 mole in 82.5 ml of benzene, prepared as in Example 1) is added dropwise at room temperature to a solution of allylamine (10 g, 0.175 mole in 100 ml of benzene). Heat is evolved and allylamine hydrochloride precipitates. After stirring overnight, the solution is diluted with ether (150 ml) and extracted with dilute hydrochloric acid (150 ml) and water (150 ml). An unidentified solid (8 g) is filtered off and discarded. The solvent is then removed to give 33.99 g. of N-allyl-2-nitro-5-(2-chloro-α,α,α-trifluoro-p-tolyloxy)benzamide as a yellow oil, which solidifies on standing. Recrystallization from isopropanol and 5% methanol gives 28.74 g. of the product amide with a melting point of 64°-68° C.

The following examples show the herbicidal properties of diphenyl ethers of the invention.

EXAMPLE 13

This example shows the herbicidal activity of diphenyl ethers of the invention towards a number of common weeds. Using the procedure described below, diphenyl ethers were evaluated for control of some or all of the following weeds:

Dicots (D)

cocklebur (*Xanthium pensylvanicum*)
marigold (Tagetes spp.)
morningglory (*Ipomoea purpurea*)
tomato (*Lycopersicon esculentum*)
velvetleaf (*Abutilon theophrasti*)

Monocots (M)

barnyardgrass (*Echinochloa crusgalli*)
downy brome (*Bromus tectorum*)
foxtail (*Setaria faberii*)
nutsedge (*Cyperus esculentus*)
wild oats (*Avena Fatua*)

The following test procedure is employed. Seeds of selected crops and weeds are planted in soil in flats. For preemergence tests, the flats are treated with the test compound immediately after the planting. For postemergence tests, the seeds are allowed to germinate, and after two weeks the flats are treated with the test compound immediately after the planting. The compound to be evaluated is dissolved in acetone, diluted with water, and sprayed over the flats using a carrier volume equivalent to 50 gallons per acre at the rate of application of two and four pounds per acre. About two weeks after the application of the test compound, the state of growth of the plants is observed and the phytotoxic effect of the compound is evaluated. The results of typical tests are summarized in Table II, which gives the average percent control achieved by the test compounds in terms of the percent of the plants which are killed by the compounds.

TABLE II

| Compound of Example No. | Rate (lb/A) | HERBICIDAL ACTIVITY | | | |
|---|---|---|---|---|---|
| | | Preemergence | | Postemergence | |
| | | M | D | M | D |
| 1 | 4 | 76 | 51 | 75 | 98 |
| | 2 | 51* | 46* | 85* | 100* |
| 2 | 4 | 87 | 98 | 68 | 99 |
| | 2 | 82 | 98 | 36 | 86 |
| 3 | 4 | 94 | 93 | 49 | 91 |
| | 2 | 76 | 85 | 45 | 85 |
| 4 | 4 | 94 | 96 | 74 | 100 |
| | 2 | 81 | 97 | 73 | 98 |
| 5 | 4 | 92 | 95 | 69 | 100 |
| | 2 | 79 | 90 | 64 | 99 |
| 6 | 4 | 87 | 90 | 22 | 96 |
| | 2 | 78 | 80 | 14 | 70 |
| 7 | 4 | 94 | 99 | 61 | 96 |
| | 2 | 84 | 98 | 51 | 92 |
| 8 | 4 | 98 | 99 | 66 | 93 |
| | 2 | 95 | 90 | 71 | 96 |
| 9 | 4 | 92 | 99 | 69 | 98 |
| | 2 | 96 | 94 | 54 | 94 |
| 10 | 4 | 96 | 99 | 68 | 100 |
| | 2 | 95 | 86 | 65 | 100 |
| 11 | 4 | 95 | 93 | 52 | 96 |
| | 2 | 94 | 90 | 34 | 99 |
| 12 | 4 | 95 | 93 | 18 | 71 |
| | 2 | 86 | 70 | 0 | 80 |

*average of two tests

Similar tests also showed tolerance of the compound of Example 1 to the following crops: corn, soybeans, wheat and rice.

EXAMPLE 14

The compounds of Example 1 to 12 were also evaluated in conventional field tests. In one typical field test, the compound of Example 1 [allyl 2-nitro-5-(2-chloro-α,α,α-trifluoro-p-tolyloxy)benzoate] was tested for control of a number of annual grasses and broadleaf weeds and for tolerance to a number of common crops. Table II summarizes these tests results.

TABLE III
FIELD TEST ACTIVITY

| Preemergence | | % Weed Control | |
|---|---|---|---|
| Rate | TEI[a] | Annual Grasses[b] | Broadleaf Weeds[c,d] |
| 0.25 | 14 | 35 | 83 |
|  | 30 | 0 | 90 |
| 1.0 | 14 | 98 | 100 |
|  | 30 | 98 | 95 |
| Postemergence | | % Weed Control | |
| Rate | TEI[a] | Annual Grasses[b] | Broadleaf Weeds[c,d] |
| 0.25 | 6 | 97 | 100 |
|  | 25 | 80 | 97 |
| 1.0 | 6 | 100 | 100 |
|  | 25 | 98 | 100 |

[a] treatment to evaluation interval (days)
[b] including crabgrass, foxtail, fall panicum
[c] preemergence including lambsquarters, ragweed, pigweed
[d] postemergence including ragweed, pigweed, purslane smartweed, galinsoga Among the crops which showed tolerance to this compound in field tests were corn, soybeans, cotton, barley and rice in preemergence application and corn, soybeans, barley and rice in postemergence applications.

In another field test, the compounds of Examples 1 to 12 were evaluated for weed control and for crop tolerance to soybeans and corn. Among the weeds which occurred naturally in or were seeded into the field test plots were velvetleaf, morningglory, sicklepod (*Cassia obtusifola*), lambsquarters (*Chenopodium album*), pigweed (*Amaranthus retroflexus*), purslane (*Portulaca oleracea*), chickweed (*Stellaria media*), and barnyardgrass.

Table III summarizes typical results from these tests.

TABLE III
FIELD TEST ACTIVITY

| Compound of Example No. | Rate (lb/A) | TEI (days) | velvet-leaf | morning-glory | sickle-pod | barn-yard-grass | lambs-quarters | pig-weed | purs-lane | chick-weed |
|---|---|---|---|---|---|---|---|---|---|---|
| 1 | 0.5 | 30 | 47 | 30 | 0 | 10 | 80 | 98 | 100 | 67 |
|   | 2   | 30 | 100 | 99 | 43 | 72 | 100 | 83 | 100 | 92 |
| 2 | 0.5 | 30 | 37 | 23 | 0 | 17 | 77 | 100 | 100 | 43 |
|   | 2   | 30 | 98 | 85 | 97 | 70 | 98 | 100 | 100 | 85 |
| 3 | 0.5 | 30 | 78 | 37 | 0 | 30 | 87 | 100 | 100 | 52 |
|   | 2   | 30 | 100 | 100 | 27 | 75 | 100 | 100 | 100 | 97 |
| 4 | 0.5 | 30 | 85 | 40 | 0 | 7 | 85 | 100 | 100 | 63 |
|   | 2   | 30 | 100 | 95 | 37 | 58 | 100 | 100 | 100 | 97 |
| 5 | 0.5 | 30 | 27 | 27 | 0 | 13 | 90 | 95 | 100 | 10 |
|   | 2   | 30 | 98 | 62 | 10 | 73 | 100 | 100 | 100 | 72 |
| 6 | 0.5 | 30 | 23 | 27 | 0 | 0 | 78 | 95 | 100 | 45 |
|   | 2   | 30 | 87 | 53 | 10 | 70 | 99 | 100 | 100 | 68 |
| 7 | 0.5 | 30 | 23 | 30 | 0 | 20 | 83 | 85 | 100 | 0 |
|   | 2   | 30 | 63 | 40 | 0 | 65 | 98 | 100 | 100 | 80 |
| 8 | 0.5 | 30 | 78 | 37 | 0 | 20 | 82 | 100 | 100 | 38 |
|   | 2   | 30 | 100 | 99 | 92 | 88 | 100 | 100 | 100 | 97 |
| 9 | 0.5 | 30 | 97 | 57 | 0 | 37 | 72 | 100 | 100 | 50 |
|   | 2   | 30 | 100 | 99 | 70 | 85 | 100 | 100 | 100 | 100 |
| 10 | 0.5 | 30 | 30 | 30 | 0 | 30 | 77 | 98 | 100 | 62 |
|    | 2   | 30 | 100 | 88 | 30 | 70 | 100 | 100 | 100 | 0 |
| 11 | 0.5 | 30 | 27 | 27 | 0 | 13 | 43 | 77 | 100 | 0 |
|    | 2   | 30 | 98 | 63 | 10 | 47 | 87 | 100 | 100 | 73 |
| 12 | 0.5 | 30 | 37 | 27 | 0 | 10 | 47 | 87 | 100 | 33 |
|    | 2   | 30 | 98 | 40 | 0 | 78 | 98 | 100 | 100 | 77 |

All of the compounds showed tolerance to soybeans and corn at the rates tested.

It is to be understood that changes and variations can be made without departing from the spirit and scope of this invention as defined by the appended claims.

What is claimed is:

1. A compound of the formula

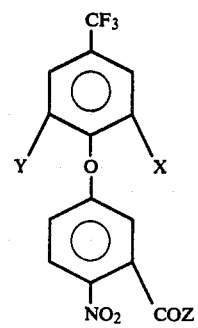

wherein
X is a hydrogen atom, a halogen atom, a trifluoromethyl group, a ($C_1$–$C_4$)alkyl group, or a cyano group,
Y is a hydrogen atom, a halogen atom, or a trifluoromethyl group, and
Z is a group of the formula —NRZ', wherein Z' is a ($C_2$–$C_6$)haloalkenyl group, a ($C_3$–$C_6$)alkynyl group, a ($C_3$–$C_6$)haloalkynyl group, a ($C_8$–$C_{12}$)aralkenyl group, a halo-, methyl-, or nitro- substituted ($C_8$–$C_{12}$)aralkenyl group, a ($C_4$–$C_7$)cycloalkenyl group, or a ($C_3$–$C_6$)epoxyalkyl group, and
R is a hydrogen atom or a ($C_1$–$C_4$)alkyl group.

2. The compound of claim 1 wherein Y is a hydrogen atom.

3. The compound of claim 2 wherein X is a halogen atom.

4. The compound of claim 3 wherein Z' is an alkenyl group.

5. The compound of claim 4 wherein Z' is an alkyl group and X is a chlorine atom.

6. The compound of claim 3 wherein Z' is an alkynyl group.

7. The compound of claim 6 wherein Z' is a propynyl group and X is a chlorine atom.

8. A herbicidal composition which comprises an effective amount of a compound according to claim 1 and an agronomically-acceptable carrier.

9. The composition of claim 8 which additionally comprises a surfactant.

10. A method of controlling weeds which comprises applying to the surface of the growth medium prior to the emergence of the weeds from the growth medium a compound of claim 1 in an amount effective to control the growth of the weeds.

11. The method of claim 10 wherein the compound is applied in an amount of about 0.1 to about 12 pounds per acre.

12. A method of controlling weeds which comprises applying to weed seedlings a compound of claim 1 in an amount sufficient to control the growth of the seedlings.

13. The method of claim 12 wherein the compound is applied in an amount of about 0.1 to about 12 pounds per acre.

* * * * *

UNITED STATES PATENT AND TRADEMARK OFFICE
CERTIFICATE OF CORRECTION

PATENT NO. : 4,209,318

DATED : June 24, 1980

INVENTOR(S) : Wayne O. Johnson

It is certified that error appears in the above—identified patent and that said Letters Patent is hereby corrected as shown below:

Column 14, line 27, after "is" insert -- a ($C_2$-$C_6$) alkenyl group,--.

Signed and Sealed this

Twenty-fifth Day of November 1980

[SEAL]

Attest:

SIDNEY A. DIAMOND

Attesting Officer

Commissioner of Patents and Trademarks

UNITED STATES PATENT AND TRADEMARK OFFICE
CERTIFICATE OF CORRECTION

PATENT NO. : 4,209,318
DATED : June 24, 1980
INVENTOR(S) : Wayne O. Johnson

It is certified that error appears in the above—identified patent and that said Letters Patent is hereby corrected as shown below:

Claim 5  After the definition of Z', delete the term "alkyl" and insert --allyl--.

Signed and Sealed this

Fourth Day of May 1982

[SEAL]

Attest:

Attesting Officer

GERALD J. MOSSINGHOFF

Commissioner of Patents and Trademarks